United States Patent [19]
Nash

[11] 4,270,903
[45] Jun. 2, 1981

[54] ABRASIVE DENTAL TOOL

[75] Inventor: John E. Nash, Downington, Pa.

[73] Assignee: Syntex Inc., Palo Alto, Calif.

[21] Appl. No.: 76,102

[22] Filed: Sep. 17, 1979

Related U.S. Application Data

[63] Continuation-in-part of Ser. No. 873,748, Jan. 30, 1978, abandoned.

[51] Int. Cl.³ ............................................. A61C 3/05
[52] U.S. Cl. .................................................. 433/165
[58] Field of Search ................. 433/168, 166; 51/204, 51/208

[56] References Cited
U.S. PATENT DOCUMENTS 3,309,772  3/1967  Lieb et al. ............................ 433/166

FOREIGN PATENT DOCUMENTS 566538  12/1932  Fed. Rep. of Germany ........... 433/165

*Primary Examiner*—Robert Peshock
*Attorney, Agent, or Firm*—John A. Dhuey; Joseph I. Hirsch

[57] ABSTRACT

A dental tool for generating a relatively smooth surface on tooth enamel comprises an elongated shank with an operative end and an end adapted to engage a chuck of a dental handpiece. Any cross-section of the operative end perpendicular to the shank's longitudinal axis is circular with a diameter of less than 0.140 inch. Adjacent, continuous annular grooves extend around the operative end, each groove being defined by a pair of inwardly sloping side surfaces intersecting with each other at least about 0.010 inch from the shank's longitudinal axis and forming an included angle of 60° to 150° between the side surfaces. An abrasive material, such as diamond grit, having a particle size of less than 0.006 inch covers at least a portion of each surface.

7 Claims, 7 Drawing Figures

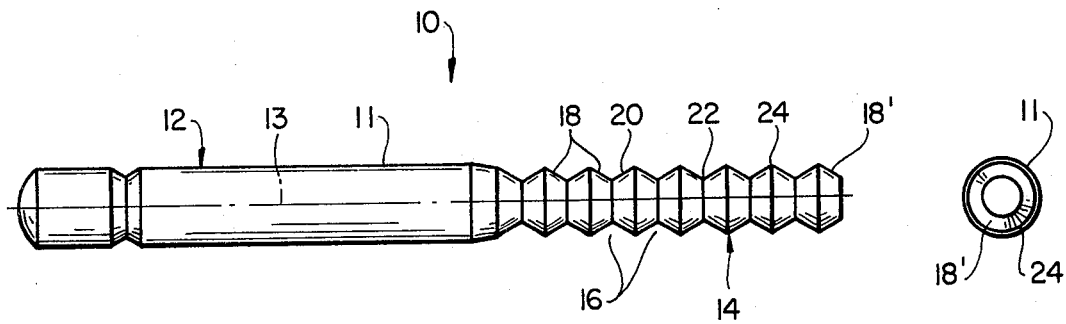
FIG_1  FIG_2
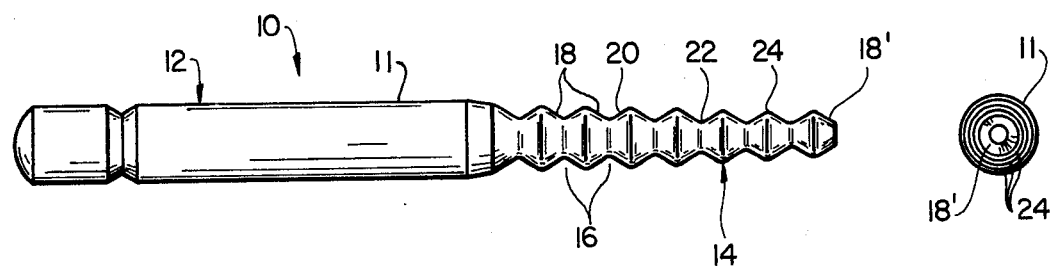
FIG_3  FIG_4
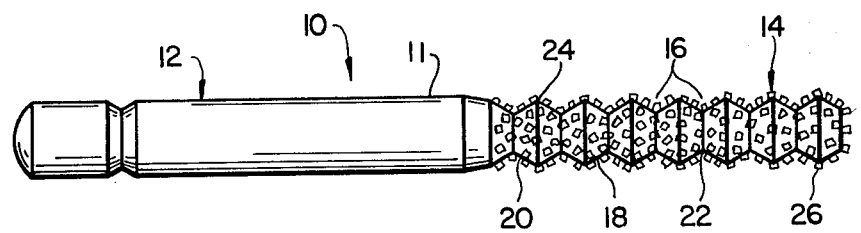
FIG_5
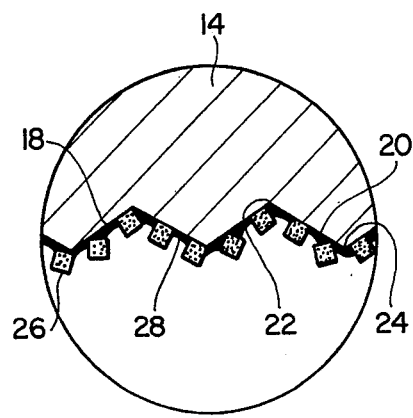
FIG_6
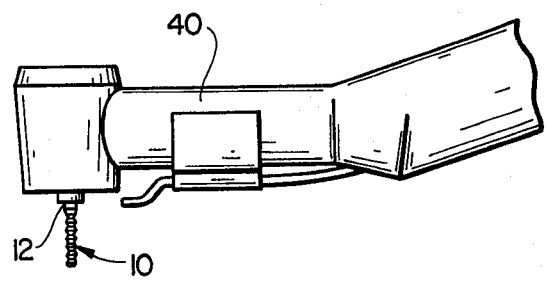
FIG_7

ABRASIVE DENTAL TOOL

RELATED APPLICATIONS

This application is a continuation-in-part of co-pending application Ser. No. 873,748, filed Jan. 30, 1978, now abandoned, the disclosure of which is incorporated herein by reference.

FIELD OF THE INVENTION

This application relates to a dental tool which is useful for grinding tooth enamel. More specifically it relates to a dental tool having a plurality of abrasive material-coated grooves in the cutting surface thereof.

PRIOR ART

Known, prior art dental burrs include, for example those shown in U.S. Pat. Nos. 482,558, 1,813,741; 2,338,437, 2,358,432, 2,606,366; 2,901,826; 3,624,095; and 3,894,339; German Pat. No. 566,538; and French Pat. No. 931,489. See also U.S. Pat. No. 4,058,898.

Other art relates to rollers for grinding, pointing and sharpening cards as in U.S. Pat. No. 4319 (1882); a cutting burr shown in U.S. Pat. No. 1,453,197; a grinding wheel for bristles shown in U.S. Pat. No. 2,017,487; and a method for making cutting blades shown in U.S. Pat. No. 2,144,987.

The dental tool of the instant invention facilitates the production of a smooth surface on the tooth by manual tracking and scanning of the tooth surface by the rapidly rotating tool. The abrasive material-coated grooves track over the tooth surface, stabilizing the tool, and the inclined surfaces permit rapid scanning of the tool over the surface with minimal bounce of the tool during the scanning motion. Use of the tool results in faster abrasion of the tooth enamel so that the dentist can perform his tasks more quickly. Also, the tool cuts "cooler" than usual dental instruments, thus causing less patient discomfort and tooth trauma.

SUMMARY OF THE INVENTION

The abrasive dental tool of this invention is of unitary construction for use with a dental handpiece and has an elongated shank having an operative end and an end adapted to engage the chuck of a dental handpiece. A cross-section of the operative end of the handpiece perpendicular to the longitudinal axis of the shank is substantially circular. A plurality of adjacent, continuous, annular grooves extend around the operative end of the shank with the plane of each annular groove being perpendicular to the longitudinal axis of the shank. Each groove has a pair of inwardly sloping side surfaces intersecting with each other at a distance of more than about 0.010 inch from the longitudinal axis of the shank while the maximum radius of the operative end of the shank is less than 0.050 inch from the longitudinal axis of the shank. The angle formed between the intersecting side surfaces of the groove is about 60° to about 150°. Covering at least a portion of the surfaces defining each groove is an abrasive material, the average particle size thereof being less than about 0.006 inches.

The tool generates a relative smooth surface upon the manual tracking and scanning thereof across the enamel surface of a tooth, and is particularly valuable for grinding tooth enamel in preparation for crown work. In this application it is to be understood that wherever the term "enamel" is used, it is intended to cover all natural tooth structure, including dentin and cementum, and all tooth restorative materials.

BRIEF DESCRIPTION OF THE DRAWINGS

The features and advantages of the present invention will become more apparent from the following detailed description taken together with the accompanying drawings wherein:

FIG. 1 is an enlarged side view of a dental tool of this invention without an abrasive material;

FIG. 2 is a right-hand end view of the tool of FIG. 1;

FIG. 3 is an enlarged side view of an alternate embodiment of the dental tool of this invention without an abrasive material wherein the diameter of the crests forming part of the operative end progressively decrease from the crest adjacent the intermediate neck of the shank toward the crest adjacent the remote end of the tool;

FIG. 4 is a right-hand end view of the tool of FIG. 3;

FIG. 5 is an enlarged side view of a dental tool of the present invention showing the abrasive material on the surfaces of the grooves;

FIG. 6 is an enlarged detail view of a portion of the operative end of FIG. 5; and FIG. 7 is a side-view of a conventional dental handpiece which is fitted with a dental tool of the present invention.

DETAILED DESCRIPTION

The abrasive dental tool of the present invention is distinguished from prior art drills, cutting instruments, and grinders both in its manner of application and critical dimensional requirements imposed because of such application. The abrasive dental tool herein described abrades natural and restorative tooth materials to produce smooth surfaces. Smooth surfaces are produced by the dual motions of "tracking", i.e. moving the tool along the tooth surface perpendicular to the longitudinal axis of the tool and by "scanning", i.e. moving the tool along the tooth surface parallel to the longitudinal axis of the tool. The "scanning" and the "tracking" capabilities of the tool, when utilized simultaneously, require a critical structure so that optimum removal of tooth material can occur without discomfort to the patient and with tactile control and feel being retained by the dental operator.

One of the difficulties encountered in producing smooth surfaces is that a grinding or cutting tool typically has a tendency to bounce when the tool is moved over the tooth surface. Bounce can be caused by cutting too deeply into the tooth surface in the "tracking" operation such that movement during the "scanning" operation is resisted by the tracks cut into the tooth surface. That problem is exemplified by dental tools such as described in U.S. Pat. No. 3,894,339 wherein a plurality of spaced grinding rings are disposed on a shaft. The sharp edges on the spaced rings tend to resist smooth continuous movement in directions parallel to the tool axis.

Cutting instruments, such as those disclosed in German Pat. No. 566,538, typically present similar problems in that the cutting edges rapidly erode tooth material to create ridges which are difficultly traversed during axial movement of the tool. Control of the tool to provide a smooth surface is difficult in view of the cutting surfaces which typically tend to bite into the tooth material rather than abrade the outermost surface.

In contrast to those instruments the abrasive tool herein described has no edges which bite deeply into the tooth material so as to cause the tool to hang up on the tooth during the scanning and tracking operation. The abrasive particles tend to wear away the surface rather than bite into it, and the inclined surfaces forming the grooves permit smooth and continuous axial movement of the tool during the scanning operation.

Because of the abrasive nature of the tool and since rapid cutting action is desired, abrasive material is applied to the inclined surfaces as well as to the crests of the grooves. In that manner, the total tool area is utilized for abrading the tooth and rapid material removal is effected without the disadvantages noted in prior art devices.

In order that "scanning" and "tracking" are optimized to produce rapid material removal while maintaining good tactile control for the dental operator, it has been determined that the crest to crest distances should be about 0.02 to 0.06 inch, abrasive particle size should be less than about 0.006 inch and average about 0.003 to 0.006 inch, and the angle formed by the intersecting side surfaces of each groove should be about 60° to about 150°.

The available area between crests permits an optimum deposit of abrasive material to effect rapid abrasion of tooth material and the angular inclinations of the interior surfaces permits tracking and scanning to produce smooth surfaces without tool bounce and with retention of tactile control by the dental operator.

A crest to crest distance which is too small will not permit sufficient deposit of abrasive material to effectuate rapid abrasion of tooth material. Also, the ability of the tool to track effectively is dependent on crest to crest distance and the depth of the grooves. Because of the stresses to which the tool is exposed during the abrading operation, it is necessary that a minimum distance of 0.01 inch be maintained between the longitudinal axis of the shank and the bottom or root of the groove.

Referring now to FIG. 1, it can be seen that dental tool 10 has an elongated shank 11 which is made of a suitable material such as stainless steel. Shank 11 has end 12 adapted to engage the chuck of a dental handpiece and an operative end 14 which has a plurality of adjacent, continuous, annular grooves 16 encircling the longitudinal axis 13 of shank 11. The length of shank 11 is such that it will readily fit a typical air driven dental handpiece, e.g. about 0.5 to about 0.8 inch long. The plane of each annular groove is perpendicular to the longitudinal axis of shank 11. Each annular groove 16 has a pair of inwardly sloping side surfaces 18 and 20 intersecting with each other at a circular, or substantially circular junction 22. Generally junction 22 will be spaced at least about 0.010 inch from the longitudinal axis 13 of shank 11 to maintain sufficient mass to withstand stresses placed thereon. The intersection 22 of surfaces 18 and 20 may be a sharp V as shown in FIG. 1 or may be slightly rounded (as shown in FIG. 3). The sides of adjacent grooves intersect to form a crest 24 which may form a sharp peak (FIG. 1) or may be slightly rounded as shown in FIG. 3. Preferably, both intersections 22 and 24 form a sharp point, i.e. "V" shaped grooves and inverted "V" shaped crests as shown in FIG. 1.

As seen in FIG. 3, an end view of operative end 12 of the dental tool perpendicular to its longitudinal axis 13 is substantially circular.

The dental tool is of unitary construction, i.e. it is manufactured from a single piece or cylinder of metal. The maximum radius of the operative end, i.e. the distance from longitudinal axis 13 to the outermost crest will be a size suitable for abrading tooth enamel. Generally, the diameter of operative end 14 is limited to about 0.14 inch (i.e. a radius of less than 0.07 inch). Because most dental handpieces accept a dental tool having a diameter of 1/16 of an inch, i.e. a radius of about 1/32 of an inch (about 0.030 inch), it is preferred that end 12 of the dental tool have a radius of 1/32 of an inch and that the maximum radius of operative end 14 will also be 1/32 of an inch, i.e. about 0.030 inch. Operative end 14 can also have a diameter less than the diameter of end 12. It is presently preferred that the largest cross-sectional dimension of end 16 perpendicular to the longitudinal axis 13 of shank 11 be equal to or greater than the longest cross-sectional dimension of operative end 14 perpendicular to longitudinal axis 13 of shank 11.

The angle formed between the intersecting sides 18 and 20 of groove 16 can be about 60° to 150°. One side 18 may be larger than the other side 20 or vice versa, but preferably the groove is a symmetrical V-shaped groove. The optimum angle between intersecting side surfaces 18 and 20 is about 120°. The distance between crests 24 of adjacent grooves is from about 0.02 inch to about 0.06 inch, but is preferably about 0.025 inch. The number of grooves provided upon the shank of the dental tool can vary from about 3 to 12 grooves per shank, but preferably will have at least 5 but no more than 10 grooves per shank.

The dental tool of this invention may be as shown in FIGS. 1 and 5 wherein the distance from the longitudinal axis to each crest 24 is the same, or the operative end of the dental tool may have a slight taper as shown in FIG. 3. In the latter case, the distance from the longitudinal axis to each crest decreases in length for each crest as one moves from left to right. Alternatively, the radial distance to each crest may first increase, then decrease to give an oval shaped longitudinal cross-section, or may vary for each crest to give an undulant longitudinal cross-section. Examples of other cutting instruments which benefit from the presence of annular grooves include spherical, football-shaped, or other convex surfaces.

Turning now to FIGS. 5 and 6, dental tool 10 has abrasive particles 26 (such as diamond, silicon carbide, boron nitride or others known in this art) covering at least a portion of the surface defining each groove. The average particle size of the abrasive particle is less than about 0.006 inch (i.e. they pass through a 100 mesh screen). The minimum size is preferably about 0.003 inches. Abrasive particles 26, are retained upon the surface of the grooves by matrix 28 using methods well known in the art.

In operation, end 12 of dental tool 10 is secured in dental handpiece 40 as shown in FIG. 7. The dentist then actuates the handpiece and contacts the tooth to be ground by tracking the rotating operative end 14 of the dental tool along the tooth surface perpendicular to the longitudinal axis of the shank and/or scanning the rotating operative end parallel to the longitudinal axis of the shank. The use of the dental tool of this invention results in faster abrasion of the tooth enamel and more stability in the abrading process than burrs known in the art, thus enabling the dentist to work more quickly and accurately. The dental tool of this invention also cuts "cooler" than usual dental burrs because the coolant can remain between the grooves. This results in less patient discomfort as well as less tooth trauma. While this invention has been described in reference to specific embodiments thereof, it should be understood by those with skill in the art that various changes can be made and equivalents may be substituted without departing from the true spirit and scope of the invention. All such modifications are intended to be within the scope of the claims appended hereto.

What is claimed is:

1. A dental tool of unitary construction for use with a dental handpiece comprising:

an elongate shank having a first operative end and a second end adapted to engage a chuck of a dental handpiece, any cross-section of said operative end perpendicular to the longitudinal axis of said shank being substantially circular, said operative end having a plurality of adjacent, continuous, substantially V-shaped annular grooves being devoid of cutting edges extending about said end, each of said grooves being formed by a pair of inclined side surfaces intersecting to form a substantially circular, lower junction lying in a plane perpendicular to the longitudinal axis of said shank, said lower junction encircling the longitudinal axis of said shank, said side surfaces intersecting side surfaces of adjacent grooves to form crests of said grooves, the included angle formed between said intersecting side surfaces being about 60° to 150°, the distance between crests of adjacent grooves being about 0.02 to 0.06 inch, and the distance from the longitudinal axis of said shank to said lower junction being greater than about 0.010 inch, and an abrasive material covering at least a portion of the surfaces defining said grooves and having a particle size of less than about 0.006 inch, said tool being adapted to generate by abrasion a relatively smooth surface upon the manual tracking and scanning thereof across the surface of a tooth.

2. The dental tool of claim 1 wherein said grooves are symmetrical V-shaped grooves.

3. The dental tool of claim 1 or 2 wherein the included angle formed between said intersecting side surfaces is about 120°.

4. The dental tool of claim 1 or 2 wherein said shank has from 3 to 12 grooves formed thereon.

5. The dental tool of claim 1 or 2 wherein the average particle size of said abrasive material is about 0.003 inch to about 0.006 inch.

6. The dental tool of claim 1 wherein the radial distance from the longitudinal axis to each crest of adjacent grooves decreases between said second end and the terminus of said first end.

7. The dental tool of claim 1 or 2 wherein the largest cross-sectional dimension of said second end perpendicular to the longitudinal axis of said shank is equal to or greater than the largest cross-sectional dimension of said first end perpendicular to the longitudinal axis of said shank.

* * * * *